United States Patent [19]

Lindner et al.

[11] 4,277,314
[45] Jul. 7, 1981

[54] ISOLATION OF 1,3-BUTADIENE FROM A C4-HYDROCARBON MIXTURE

[75] Inventors: Alfred Lindner, Bobenheim-Roxheim; Klaus Volkamer, Frankenthal; Ulrich Wagner, Limburgerhof, all of Fed. Rep. of Germany

[73] Assignee: BASF Aktiengesellschaft, Fed. Rep. of Germany

[21] Appl. No.: 40,283

[22] Filed: May 18, 1979

[30] Foreign Application Priority Data

Jun. 1, 1978 [DE] Fed. Rep. of Germany ....... 2823983

[51] Int. Cl.³ .............................................. B01D 3/40
[52] U.S. Cl. ....................................... 203/50; 203/82; 203/84; 203/98; 585/808
[58] Field of Search .................... 260/681.5 R, 677 A; 585/800, 833, 807, 808, 802, 803, 809, 810, 901; 203/57, 58, 98, 59, 61, 62, 50, 71, 81, 82, 84

[56] References Cited

U.S. PATENT DOCUMENTS 3,772,158  11/1973  Sarno ..................................... 203/58
3,798,132   3/1974  Sarno ..................................... 203/58

FOREIGN PATENT DOCUMENTS 1378385 12/1974 United Kingdom .

Primary Examiner—Frank Sever
Attorney, Agent, or Firm—Keil & Witherspoon

[57] ABSTRACT

A process for isolating 1,3-butadiene by means of a selective solvent from a C4-hydrocarbon mixture which contains 1,3-butadiene, propyne, hydrocarbons which are more soluble than 1,3-butadiene in the selective solvent and hydrocarbons which are less soluble than 1,3-butadiene in the selective solvent, wherein the C4-hydrocarbon mixture is separated, using one or more extractive distillation zones, into a distillate containing the less soluble hydrocarbons, a stream of 1,3-butadiene and a stream containing the more soluble hydrocarbons, and the propyne is separated off either by distillation of the C4-hydrocarbon mixture in a distillation zone upstream of the extractive distillation zone or zones or by distillation of the stream of 1,3-butadiene, obtained from the extractive distillation zone or zones, in a downstream distillation zone, giving a stream of hydrocarbons containing propyne and 1,3-butadiene, which stream is fed to an additional distillation zone, while at the same time a second stream of liquid or gaseous hydrocarbons is fed to the additional distillation zone, and the bottom product from the additional distillation zone is recycled to the extractive distillation.

4 Claims, 1 Drawing Figure

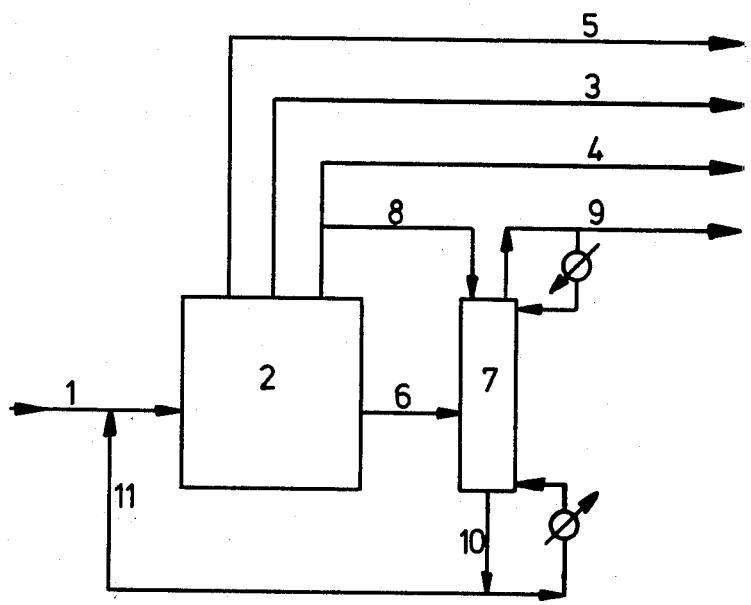

ISOLATION OF 1,3-BUTADIENE FROM A C4-HYDROCARBON MIXTURE

The present invention relates to a process for isolating 1,3-butadiene from a $C_4$-hydrocarbon mixture containing 1,3-butadiene and small amounts of propyne.

It is known, for example from British Pat. No. 1,378,385, to isolate 1,3-butadiene from a $C_4$-hydrocarbon mixture containing 1,3-butadiene and small amounts of propyne by separating the $C_4$-hydrocarbon mixture by extractive distillation with a selective solvent, giving a 1,3-butadiene which still contains a large part of the propyne which was present in the initial $C_4$-hydrocarbon mixture. The 1,3-butadiene containing propyne is therefore additionally distilled to remove the propyne. However, because of the tendency of propyne to suffer auto-decomposition, safety reasons dictate that when distilling the propyne-containing 1,3-butadiene, only a propyne distillate with 1,3-butadiene and containing about 50% by volume of propyne should be taken off, leading to substantial losses of 1,3-butadiene. To reduce these losses, the propyne distillate diluted with 1,3-butadiene is recycled, in the conventional process, to the distillation section of an ethylene plant.

However, this process is unsatisfactory, particularly since it can only be carried out if an ethylene plant is available in the vicinity of the butadiene plant. Another possible method of removing the propyne is to subject the initial $C_4$-hydrocarbon mixture, containing small amounts of propyne, prior to the extractive distillation, to a distillation in which a propyne distillate diluted by $C_3$- and $C_4$- hydrocarbons is taken off. This method requires a high bottom temperature and a high operating pressure in order to be able to effect condensation at the top of the column by means of cooling water. However, a high bottom temperature favors the thermal dimerization, and the polymerization, of butadiene.

It is an object of the present invention to improve the method and economics of the conventional processes.

More particularly, it is an object of the present invention to provide a process for isolating butadiene, by means of a selective solvent, from a propyne-containing $C_4$-hydrocarbon mixture, in which process the propyne can be separated off in a simple manner, without substantial losses of butadiene.

We have found that these and other objects and advantages are achieved, according to the invention, by a process for isolating 1,3-butadiene by means of a selective solvent from a $C_4$-hydrocarbon mixture which contains 1,3-butadiene, propyne, hydrocarbons which are more soluble than 1,3-butadiene in the selective solvent and hydrocarbons which are less soluble than 1,3-butadiene in the selective solvent, wherein the $C_4$-hydrocarbon mixture is separated, using one or more extractive distillation zones, into a distillate containing the less soluble hydrocarbons, a stream of 1,3-butadiene and a stream containing the more soluble hydrocarbons, and the propyne is separated off either by distillation of the $C_4$-hydrocarbon mixture in a distillation zone upstream of the extractive distillation zone or zones or by distillation of the steam of 1,3-butadiene, obtained from the extractive distillation zone or zones, in a downstream distillation zone, giving a stream of hydrocarbons containing propyne and 1,3-butadiene, which stream is fed to an additional distillation zone, whilst at the same time a second stream of liquid or gaseous hydrocarbons is fed to the additional distillation zone, and the bottom product from the additional distillation zone is recycled to the extractive distillation.

Using the novel process, it is possible to obtain 1,3-butadiene in substantially greater yield from a $C_4$-hydrocarbon mixture containing propyne than when using the conventional processes, but no increased safety hazard is entailed. Furthermore, the distillation column from which the hydrocarbon stream containing propyne and 1,3-butadiene is obtained can be operated at a lower bottom temperature, so that the risk of polymerization is reduced.

The propyne-containing $C_4$-hydrocarbon mixtures to be employed, according to the invention, for the isolation of 1,3 -butadiene are obtained as a hydrocarbon fraction in, for example, the manufacture of ethylene and/or propylene by thermal cracking of a petroleum fraction, for example of liquefied petroleum gas (LPG), naphtha, gas oil and the like. Further, such $C_4$-fractions are obtained on catalytic dehydrogenation of n-butane and/or n-butene. The $C_4$-hydrocarbon mixture as a rule contains butanes, n-butene, isobutene, 1,3-butadiene, vinylacetylene, ethylacetylene, 1,2-butadiene and propyne and may contain small amounts of $C_5$-hydrocarbons. The propyne content of the $C_4$-hydrocarbon mixtures is as a rule from 0.001 to 1% by weight, mostly from 0.005 to 0.5% by weight. However, the process according to the invention is also applicable to $C_4$-hydrocarbon mixtures of higher propyne content, eg. to $C_4$-hydrocarbon mixtures with propyne contents of from 0.001 to 10% by weight, preferably from 0.005 to 5% by weight.

Examples of suitable selective solvents are carboxylic acid amides, eg. dimethylformamide, diethylformamide, dimethylacetamide, formylmorpholine, acetonitrile, furfurol, N-methylpyrrolidone, butyrolactone, acetone and mixtures of these with water. The use of N-methylpyrrolidone as the selective solvent is particularly advantageous.

Examples of hydrocarbons which are more soluble than 1,3-butadiene in the selective solvent are vinylacetylene, ethylacetylene and 1,2-butadiene. Examples of hydrocarbons which are less soluble than 1,3-butadiene in the selective solvent are the butanes, the n-butenes and isobutene.

The extractive distillation can be carried out using one extractive distillation zone. However, the process for isolating 1,3-butadiene is particularly advantageously carried out using two successive extractive distillation zones, the same selective solvent being used in both. For example, in the first stage of the extractive distillation a distillate (raffinate) containing the less soluble hydrocarbons, and an extract containing 1,3-butadiene, the more soluble hydrocarbons and the selective solvent are obtained. The extract is freed from the selective solvent, giving a mixture of 1,3-butadiene and the more soluble hydrocarbons. In a second extractive distillation zone, this mixture is subjected to a second extractive distillation with the selective solvent, giving 1,3-butadiene as the distillate and an extract which contains the more soluble hydrocrbons, including the higher acetylenes, any residual 1,3-butadiene, and the selective solvent. The extract obtained is subsequently freed from the selective solvent, giving a hydrocarbon stream which contains the more soluble hydrocarbons, including the $C_4$-acetylenes.

The propyne is separated off either by distilling the initial $C_4$-hydrocarbon mixture in a distillation zone upstream of the extractive distillation, or by distilling the propyne-containing 1,3-butadiene stream, obtained after extractive distillation, in a distillation zone downstream of the extractive distillation, the distillate obtained, advantageously as the top product of the distillation, being a hydrocarbon mixture containing 1,3-butadiene and propyne. For safety reasons, the distillate in general has a propyne content of at most 70 mole %, preferably at most 60 mole %, and in particular at most 50 mole %.

The hydrocarbon mixture which is obtained from the distillation zone upstream or downstream of the extractive distillation and which contains propyne and 1,3-butadiene is subsequently fed to an additional distillation zone and at the same time a second stream of liquid or gaseous hydrocarbons is fed to the additional distillation zone.

The liquid or gaseous hydrocarbons fed as a second stream to the additional distillation zone are in general $C_3$- and/or $C_4$-hydrocarbons, preferably saturated and/or monoolefinically unsaturated $C_3$-and/or $C_4$hydrocarbons. Advantageously, these hydrocarbons are used in the form of mixtures, for example as $C_3$- and/or $C_4$-hydrocarbon mixtures. Examples of suitable hydrocarbons are propane, propene, the butanes, n-butene, isobutene and their mixtures. It is advantageous to use $C_4$-hydrocarbon mixtures. In a preferred embodiment of the process, the distillate (raffinate) which is obtained in the first extractive distillation zone and which contains butanes and butenes is used.

The second stream of hydrocarbons fed to the additional distillation zone can first be mixed with the hydrocarbon stream containing propyne and 1,3-butadiene and then be fed to the additional distillation zone to undergo conventional distillation. Preferably, however, the second hydrocarbon stream is fed to the additional distillation zone at or advantageously above the feed point of the hydrocarbon stream containing propyne and 1,3-butadiene, preferably in the upper quarter, in particular at the top, of the additional distillation zone. By feeding in the second hydrocarbon stream above the feed point of the hydrocarbon stream containing propyne and 1,3-butadiene, particularly advantageous separation of the propyne and 1,3-butadiene is achieved due to the resulting counter-current wash, so that a bottom product of high 1,3-butadiene concentration is obtained whilst the steam consumption for the separation is relatively low. In a preferred embodiment of the process according to the invention, the second hydrocarbon stream is admixed to the liquid reflux of the distillation zone, or is introduced in place of a liquid reflux.

Advantageously, the hydrocarbon stream containing propyne and 1,3-butadiene is fed into the additional distillationzone in a middle region, extending from the middle of the distillation zone to the extent of about 80%, preferably of about 60%, especially of about 50%, into both the upper and lower half of the additional distillation zone. The hydrocarbon stream containing propyne and 1,3-butadiene, and the second hydrocarbon stream, can be fed to the additional distillation zone as a gas or liquid, the latter being preferred. In general, the weight ratio of hydrocarbons in the second hydrocarbon stream to hydrocarbons of the stream containing propyne and 1,3-butadiene is from 10:1 to 1:10, preferably from 5:1 to 1:5, especially from 2:1 to 1:2. In general, conventional distillation columns, for example packed columns or tray columns, are used for the additional distillation zone. By using the method according to the invention, the top product obtained from the additional zone is a distillate containing propyne, the content of the latter being advantageously at most 70 mole %, preferably at most 60 mole %, in particular at most 50 mole %, and at the same time having a substantially reduced butadiene content, for example of at most 10% by weight, preferably at most 5% by weight, so that the loss of 1,3-butadiene during isolation of the latter is substantially diminished.

The bottom product of the additional distillation zone, which contains the greater part of the 1,3-butadiene fed to the additional distillation zone, is recycled to the extractive distillation. Advantageously, the bottom product is admixed to the initial $C_4$-hydrocarbon mixture fed to the first extractive distillation zone.

The FIGURE presents a schematic diagram of an embodiment of the novel process.

A $C_4$-hydrocarbon mixture containing, 1,3-butadiene and small amounts of propyne (the mixture being a $C_4$-fraction from an ethylene plant) is fed through line 1 into a butadiene isolation plant 2, where it is first separated, in two successive extractive distillation zones, using a selective solvent (N-methylpyrrolidone), into a stream 3 containing the $C_4$-acetylenes, a raffinate stream 4 containing the butanes and butenes, and a stream of 1,3-butadiene, after which the last-mentioned stream is further separated, in a distillation column, into a very pure 1,3-butadiene stream 5, obtained as the bottom product, and a propyne/1,3-butadiene stream 6 obtained as the top product of the distillation column. The propyne/1,3-butadiene stream is fed into the middle third of a packed column 7, whilst a small part-stream 8 is branched off the raffinate stream 4 and fed to the top of column 7. At the top of column 7, a hydrocarbon stream 9 containing the propyne and only a small amount of 1,3-butadiene is taken off. At the bottom of column 7, a hydrocarbon stream 10 having a high 1,3-butadiene content, with only slight traces of propyne, is taken off and recycled to the extractive distillation through line 11.

The Examples which follow further illustrate the invention.

EXAMPLE 1

In a 1,3-butadiene isolation process, comprising two successive extractive distillations and a downstream distillation column, a mixture of 50% by volume of 1,3-butadiene and 50% by volume of propyne is obtained as the top product of the distillation column.

100 g/h of this propyne/1,3-butadiene mixture are fed in at the 28th tray of a 45 tray column. At the top of the column, 80 g/h of a raffinate which is obtained from the isolation of 1,3-butadiene and essentially consists of butane, iso-butane, 1-butene, iso-butene, trans-2-butene, cis-2-butene, propane and propene is fed in. Sufficient heat is supplied to the bottom of the column to give a reflux of 99.2 g/h. At the top of the column, 102 g/h of a hydrocarbon stream containing only 5.7% by weight of 1,3-butadiene and 41.7% by weight of propyne are taken off. At the bottom, 78 g/h of a hydrocarbon stream comprising 66.4% by weight of 1,3-butadiene and 33.6% by weight of a mixture of $C_3$- and $C_4$-hydrocarbons are taken off and recycled to the extractive distillation. The bottom product contains only 36 ppm by weight of propyne. At no point of the column is a propyne concentration of 50% by volume exceeded. This limit was imposed in order to maintain conditions sufficiently remote from the autodecomposition threshold of propyne.

EXAMPLE 2

If the procedure described in Example 1 is followed, but the amount of raffinate fed in is increased to 150 g/h and the amount of reflux to 180 g/h, the butadiene content in the top product can be reduced to 1% by weight.

At the bottom, 148 g/h of a mixture of 38.4% by weight of 1,3-butadiene and 61.6% by weight of $C_3$- and $C_4$-hydrocarbons are taken off. The bottom product contains 115 ppm by weight of propyne and throughout the column the propyne concentration is less than 50% by volume.

We claim:

1. A process for isolating 1,3-butadiene by means of a selective solvent from a $C_4$-hydrocarbon mixture which contains 1,3-butadiene, propyne, hydrocarbons which are more soluble than 1,3-butadiene in the selective solvent and hydrocarbons which are less soluble than 1,3-butadiene in the selective solvent, which process comprises:
   a. subjecting the $C_4$-hydrocarbon mixture to extractive distillation in a butadiene isolation plant, wherein the $C_4$-hydrocarbon mixture is separated into a distillate containing the hydrocarbons less soluble than 1,3-butadiene, a stream containing 1,3-butadiene and propyne, and a stream containing the hydrocarbons more soluble than 1,3-butadiene,
   b. distilling the stream containing 1,3-butadiene and propyne in a distillation zone downstream of the extractive distillation in the butadiene isolation plant to obtain a stream of 1,3-butadiene which is recovered and as a distillate a hydrocarbon mixture containing 1,3-butadiene and the propyne,
   c. subjecting the distillate from the downstream distillation zone to distillation in an additional distillation zone, said distillate being fed into the additional distillation zone in a middle region, extending from the middle of the additional distillation zone to the extent of about 80% into both the upper and lower half of the additional distillation zone,
   d. feeding at the same time a second stream of liquid or gaseous hydrocarbons to the additional distillation zone at or above the feed point of the distillate from the downstream distillation zone, obtaining as overhead from the additional distillation zone a propyne-containing hydrocarbon mixture having a 1,3-butadiene content of not more than 10% by weight, and
   e. recycling the 1,3-butadiene-containing bottom product only from the additional distillation zone to the extractive distillation zone solely within said butadiene isolation plant.

2. A process as claimed in claim 1, wherein a mixture of $C_3$- and/or $C_4$-hydrocarbons is fed, as said second stream, to the additional distillation zone.

3. A process as claimed in claim 1, wherein a saturated or monoolefinically unsaturated $C_4$-hydrocarbon, or a mixture of such hydrocarbons, is fed as said second stream to the additional distillation zone.

4. A process as claimed in claim 1, wherein the feed point of said second stream is in the upper third of the additional distillation zone.

* * * * *